(12) United States Patent
Solomon et al.

(10) Patent No.: US 9,700,451 B2
(45) Date of Patent: *Jul. 11, 2017

(54) MAGNETORHEOLOGICAL MEDICAL BRACE

(71) Applicants: Clifford T. Solomon, Hempstead, MD (US); Theodore C. Solomon, Hempstead, MD (US)

(72) Inventors: Clifford T. Solomon, Hempstead, MD (US); Theodore C. Solomon, Hempstead, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/066,849

(22) Filed: Mar. 10, 2016

(65) Prior Publication Data

US 2016/0184125 A1    Jun. 30, 2016

Related U.S. Application Data

(63) Continuation of application No. 14/228,620, filed on Mar. 28, 2014, now Pat. No. 9,283,103, which is a
(Continued)

(51) Int. Cl.
*A61F 5/00* (2006.01)
*A61F 5/01* (2006.01)
(Continued)

(52) U.S. Cl.
CPC .......... *A61F 5/0104* (2013.01); *A61F 5/0106* (2013.01); *A61N 2/004* (2013.01); *A61N 2/02* (2013.01); *A61N 2/06* (2013.01)

(58) Field of Classification Search
CPC .......... A61N 2/004; A61N 2/008; A61N 2/02; A61N 2/06
See application file for complete search history.

(56) References Cited

U.S. PATENT DOCUMENTS 2,802,463 A * 8/1957 Simjian .................. A61F 13/04
                                                    264/220
5,382,373 A * 1/1995 Carlson .................. H01F 1/447
                                                    252/62.52
(Continued)

FOREIGN PATENT DOCUMENTS

CN      101251164 A     8/2008
DE    198 20 570 A1    11/1999
(Continued)

OTHER PUBLICATIONS

Ahmadkhanlou, F. "A passive and a semi-active orthopedic knee brace," The Ohio State University, http://etd.ohiolink.edu/send-pdf.cgi/Ahmadkhanlou%20Farzad.pdf?osu1212419874.
(Continued)

*Primary Examiner* — Kim M Lewis
(74) *Attorney, Agent, or Firm* — Seed IP Law Group LLP

(57) ABSTRACT

The magnetorheological (MAR) medical brace includes a flexible outer shell that fits around the anatomical area to be braced and a plurality of adjustable straps for securing the shell onto the anatomical area. The shell encases a MAR pack filled with magnetorheological fluid or gel. A plurality of magnets is attached to or encased in the shell to provide magnetic field acting on the MAR pack. The interaction of the magnetic field with the MAR pack adjustably increases or decreases the stiffness of the shell depending on the strength of the magnetic field. A control mechanism is provided for selective adjustment of the magnetic field and other functions.

3 Claims, 6 Drawing Sheets

Related U.S. Application Data continuation of application No. 13/556,112, filed on Jul. 23, 2012, now Pat. No. 8,696,610.

(60) Provisional application No. 61/510,432, filed on Jul. 21, 2011.

(51) Int. Cl.
*A61N 2/00* (2006.01)
*A61N 2/02* (2006.01)
*A61N 2/06* (2006.01)

(56) References Cited

U.S. PATENT DOCUMENTS

| | | | |
|---|---|---|---|
| 7,393,364 B2 | 7/2008 | Martin | |
| 7,455,696 B2 | 11/2008 | Bisbee, III et al. | |
| 7,507,215 B2 | 3/2009 | Ryan | |
| 7,659,636 B2 | 2/2010 | Donelan et al. | |
| 7,691,154 B2 | 4/2010 | Asgeirsson et al. | |
| 7,892,630 B1 | 2/2011 | McKnight et al. | |
| 8,277,402 B2 | 10/2012 | Chisena et al. | |
| 8,579,842 B2 | 11/2013 | Majidi et al. | |
| 8,696,610 B2 * | 4/2014 | Solomon | A61N 2/004 600/15 |
| 9,078,774 B2 * | 7/2015 | Jonsson | A61F 2/6607 |
| 9,283,103 B2 * | 3/2016 | Solomon | A61N 2/004 |
| 2004/0002665 A1 | 1/2004 | Parihar et al. | |
| 2004/0126565 A1 | 7/2004 | Naganathan et al. | |
| 2005/0011710 A1 * | 1/2005 | Hitchcock | F16F 1/361 188/267.2 |
| 2007/0282230 A1 * | 12/2007 | Valderrabano | A61F 5/0104 601/152 |
| 2008/0065230 A1 | 3/2008 | Nordt et al. | |
| 2008/0083140 A1 | 4/2008 | Ellis | |
| 2008/0300692 A1 | 12/2008 | Moser et al. | |
| 2009/0030530 A1 | 1/2009 | Martin | |
| 2010/0251574 A1 | 10/2010 | Battlogg et al. | |
| 2011/0054330 A1 | 3/2011 | Pfeiffer et al. | |
| 2012/0035410 A1 | 2/2012 | Borgos et al. | |

FOREIGN PATENT DOCUMENTS

| | | |
|---|---|---|
| KR | 2002-0067440 | 8/2002 |
| KR | 2007-012148 | 11/2007 |

OTHER PUBLICATIONS

Ahmadkhanlou, F. "Design, Modeling and Control of Magnetorheological Fluid-Based Force Feedback Dampers for Telerobotic Systems"; The Ohio State University, http://etd.ohiolink.edu/send-pdf.cgi/Ahmadkhanlou%20Farzad.pdf?osu1212419874; 2008.

Leg Brace with MR Fluid Brake, Dig Info TV; Website: http//www.diginfo.tv/2010/10/22/10-0202-4-en.php; Oct. 22, 2010.

* cited by examiner

MAGNETORHEOLOGICAL MEDICAL BRACE

CROSS-REFERENCE TO RELATED APPLICATIONS

This application is a continuation of U.S. patent application Ser. No. 14/228,620, filed Mar. 28, 2014, which is a continuation of U.S. patent application Ser. No. 13/556,112, filed Jul. 23, 2012, now U.S. Pat. No. 8,696,610, which claims the benefit of U.S. Provisional Application No. 61/510,432, filed Jul. 21, 2011, all of which are hereby incorporated by reference in their entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNOLOGY FIELD

This disclosure relates to medical devices and particularly to a magnetorheological medical brace with controlled stiffness for optimal support and recovery.

DESCRIPTION OF THE RELATED ART

Any type of trauma or injury to a limb or bone requires a relatively long time to heal. In many cases, the physician usually recommends at least six weeks of recovery time. To ensure proper recovery, the limb or bone is immobilized either by braces, splints or a cast depending on the extent of damage. This stabilizes the bone or limb so as to prevent, in the case of broken bones, undesirable misalignment of the set bone or in the case of sprains or other types of injuries, any movement that may cause further injury or unnecessary pain. While such measures are quite sufficient, the immobilized limb and the surrounding muscles tend to atrophy due to lack of physical movement. It is not unusual for a patient to struggle through a post-recovery regimen of physical exercise or therapy in order to gain the prior musculature and strength in the injured anatomy.

Another complication to such healing is a matter of comfort and convenience. As the patient endures the period of healing, the recovering area tends to itch, which is usually a positive symptom that recovery is going well. However, for some types of braces, it may be challenging for the patient to reach the agitated area to scratch, which often ends in frustration and irritation. For some, it may even reach unendurable proportions such that the patient is forced to remove the brace, splint or cast, which can jeopardize the healing progress. Moreover, attempts to clean the injured limb can be challenging. Since removal of the brace, splint or cast prior to complete healing is not usually recommended, the patient typically forgoes cleaning of the injured area during the period of recovery. This can lead to unsightly accumulation of dirt and grime or potential infections, especially for patients who had undergone surgery for the injury.

In order to accelerate healing, re-strengthening of the injured area and increase comfort and convenience for the patient, it would be more effective for a brace, splint or cast to be progressively loosened during the period of recovery such that the patient has some limited movement for exercising the limb as the limb heals, at least for a relatively short period of time. This can be conventionally facilitated by frequent visits to the health care facility for doctor consultation and replacement or adjustment of the medical device. However, frequent visits can be costly in terms of finances and time.

Sports braces such as those for the joints, e.g., ankles, wrists, knees and elbows, also suffer from similar effectiveness deficiencies. Most sports braces do not have any means of selectively increasing or decreasing the stiffness of the brace. The inherent stiffness of a prescribed sports brace may be sufficient for most, but it could be problematic for those suffering from weak joints or other joint related complications. For example, the stiffness of the brace may dramatically hinder movement, which decreases the benefits of the sports activity and/or the enjoyment thereof. Moreover, as time passes, the user may require more or less support from the brace due to extended movement of the joint or from physical expenditure.

In light of the above, it would be a benefit in the medical arts to provide an immobilizing device with adjustable stiffness for more effective healing, support, convenience and comfort. Thus, a magnetorheological medical brace having easily adjustable stiffness is needed to solve the aforementioned problems.

SUMMARY

Briefly, and in general terms, the claimed Magnetorheological (MAR) medical brace includes a flexible outer shell that fits around the anatomical area to be braced. The shell encases a MAR pack filled with magnetorheological fluid or gel. A plurality of magnets is attached to or encased in the shell to provide a magnetic field acting on the MAR pack. The interaction of the magnetic field with the MAR pack adjustably increases or decreases the stiffness of the shell depending on the strength of the magnetic field. A control mechanism may be provided for selective adjustment of the magnetic field and other functions.

These and other features of the medical device will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
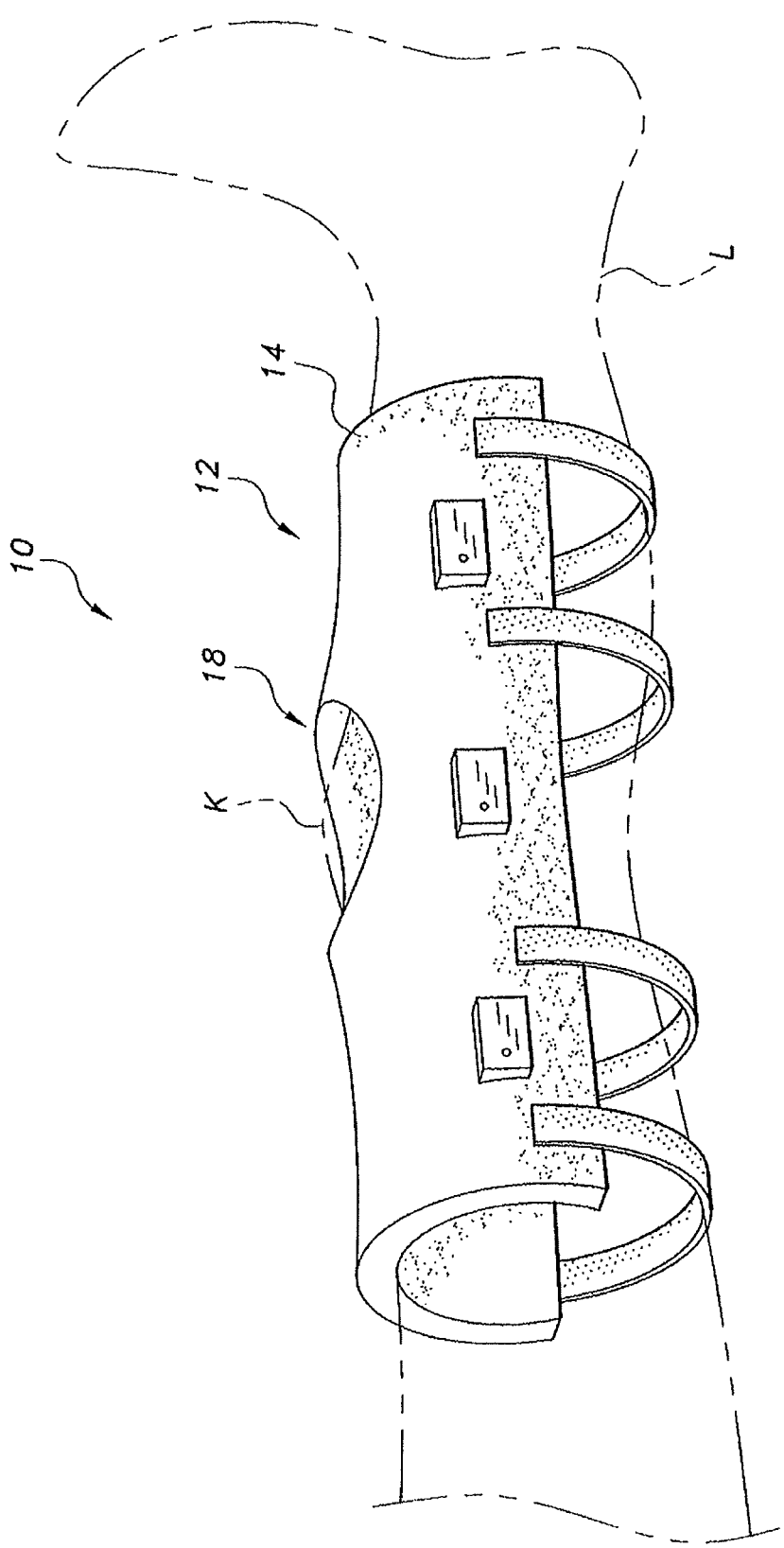
FIG. 1 is an environmental, perspective view of a magnetorheological medical brace.
Figure 2:
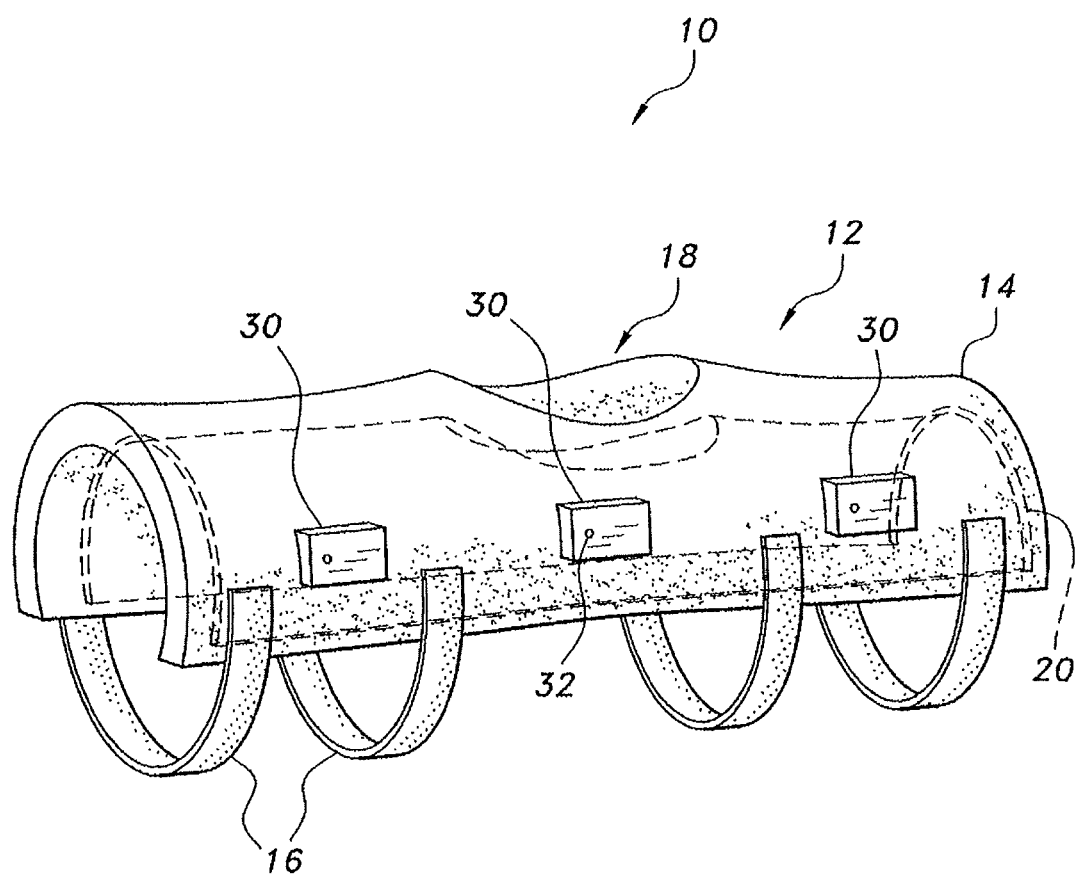
FIG. 2 is a perspective view of the magnetorheological medical brace.

The magnetorheological medical brace, a first embodiment of which is generally referred to by the reference number 10, provides adjustable stiffness and other features for optimum support, convenience and comfort. The phrase "magnetorheological medical brace" will hereinafter be referred to as "MAR medical brace." In the exemplary embodiment shown in FIGS. 1 and 2, the MAR medical brace 10 may be a leg brace 12 having an elongate shell or cover 14 adapted to be wrapped around the user's leg L. The shell 14 is substantially semi-cylindrical or semi-frustoconical in shape so that the shell 14 may easily wrap around and conform to the anatomy of leg L. The shell 14 is also relatively stiff or rigid to provide minimum support, as well as to retain the general shape of the shell 14. However, the shell 14 should also be flexible to allow for some movement without much effort. The shell 14 may be constructed from resilient, polymeric foam with some relative stiffness for minimum rigidity. Other materials such as neoprene, cushioned mats, elastomers, steel, plastics and combinations thereof may also be used as needed for some components of the brace.

The shell 14 can include a central through hole 18 where a patient's or user's knee joint K may protrude. The hole 18 permits flexing of the knee without encumbrance. A plurality of adjustable attachment connectors, such as straps 16, may be disposed at spaced intervals along the length of the shell 14. These straps 16 secure the shell 14 onto a wide range of leg girths. The straps 16 may be secured to the user by hook and loop fasteners, buckles, snap-fit fasteners or any other type of adjustable connectors.

To facilitate adjustable stiffening of the leg brace 12, the shell 14 includes a magnetorheological (MAR) cell, tube or pack 20 disposed inside the shell 14. The MAR pack 20 is preferably a packet or durable balloon filled with magnetorheological material in fluid or gel form. MAR material is a substance that can vary the material yield stress characteristics when exposed to a magnetic field. In other words, the stillness or rigidity of the MAR pack 20 varies, depending on the strength of magnetic forces acting thereon. Thus, whenever the MAR pack 20 experiences some degree of magnetic force or field, the whole leg brace 12 correspondingly stiffens or loosens proportionately to the overall rigidity of the MAR pack 20. One example of such a MAR material is a combination of carbonyl iron powder and silicone oil. It is to be understood that other MAR materials may also be used for the MAR pack 20. In the preferred embodiment, the leg brace 12 is of unitary construction formed in a molding process with the MAR pack 20 embedded within the shell 14. As an alternative, the MAR pack 20 may be removably inserted inside a cavity within the shell 14.

The magnetic force or field may be supplied by a plurality of magnet packs, consoles or terminals 30 disposed on one or both sides of the leg brace 12. Each magnet pack 30 can include a permanent magnet or an electromagnet of a given strength. In a preferred embodiment, the magnet packs 30 are magnetically shielded on the outside to ensure that magnetic forces influence the MAR material, rather than anything else that may be nearby. When using permanent magnets, the physician or the user may selectively change one for another of higher or lower strength to adjust the of stiffness of the MAR medical brace 10. Similar results may be obtained with an electromagnet by using a control mechanism to adjust the magnetic field strength, an example of which will be described below.

Figure 6:
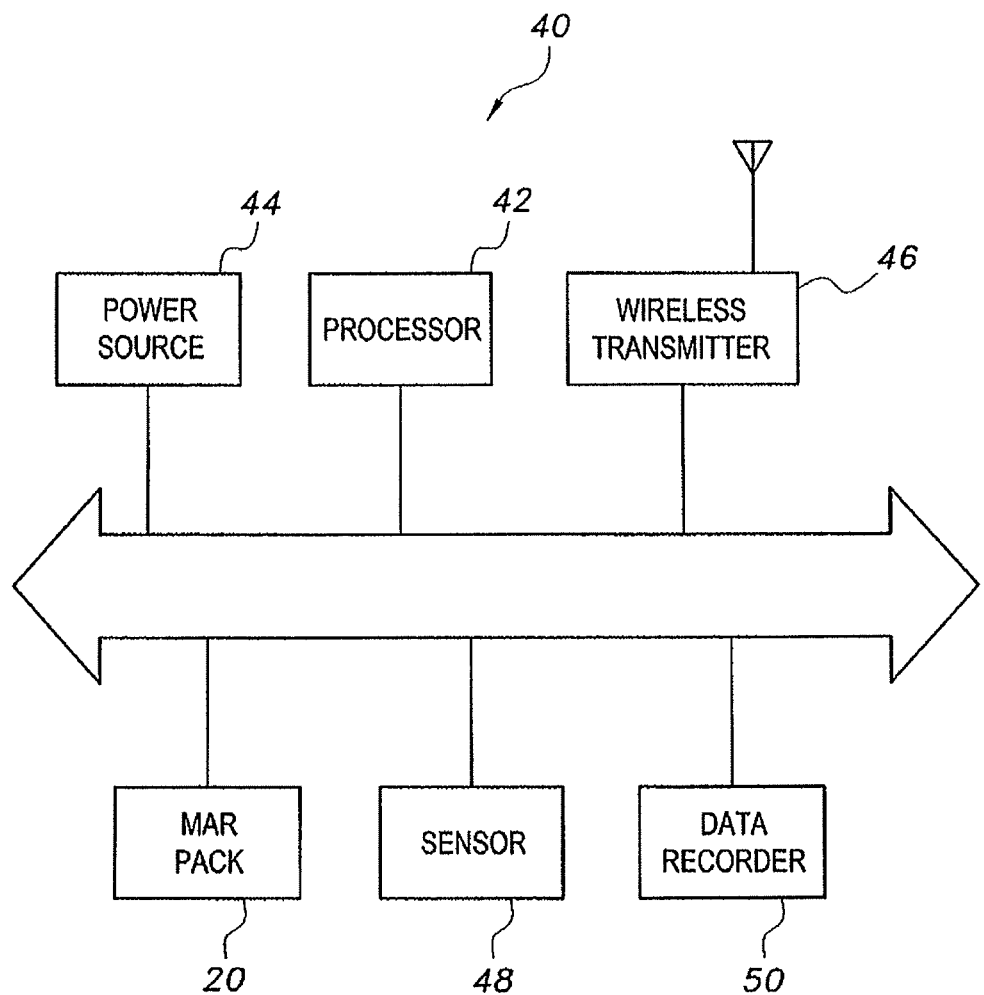
FIG. 6 is a schematic diagram of the controls for a magnetorheological medical brace.

In the preferred embodiment, the control mechanism 40 may be disposed in one of the magnet packs 30. As shown schematically in FIG. 6, the control mechanism 40 includes a processor 42 for controlling the various functions of the control mechanism 40 and is connected to a power source 44 supplying power to the control assembly 40 and the electromagnets in the other magnet packs 30. In a preferred embodiment, the power source 44 can be a rechargeable and reusable battery, such as lead-acid, nickel cadmium (NiCd), nickel metal hydride (NiMH), lithium ion (Li-ion), and lithium ion polymer (Li-ion polymer). As an alternative, the power may be supplied directly from an AC source. To adjust the strength of the electromagnet, the user can increase or decrease the amount of power being supplied to the MAR pack 20 via the processor 42 to thereby selectively strengthen or weaken the magnetic field. The magnet pack 30 may include an indicator light or display 32 that provides information about the operations of the control mechanism 40, e.g., ON, OFF and/or remaining power.

In addition to the basic control of the magnetic field or force, the control mechanism 40 includes other features to help monitor the patient's or user's healing and/or exercise progress. The control mechanism 40 can include a sensor 48 that senses various activities such as the frequency of wear, the intensity of the magnetic field, the frequency of limb movement, and the like. This data may be recorded on the data recorder 50 and transmitted wirelessly via a wireless transceiver 46 to a monitoring station, such as a central database in a health care facility or to a personal computer. The recorded and transmitted data helps the physician or user calculate and determine physical activity goals. Moreover, the data may be used to monitor the user's adherence with the physician's recommendations. For example, if the physician prescribed a strict guideline and duration of wearing the leg brace 12 and the patient fails to comply, as evidenced by prolonged periods of recorded inactivity, the transmitted data will note the lapse and alert the physician. Then the physician may follow up with the patient in a timely manner to determine the cause. As an alternative, the data stored in the data recorder 50 may be retrieved at the end of a given period of time instead of being transmitted by the wireless transceiver 46, especially for those who live in areas where wireless communication is not available.

Data transmission and the data itself may be compromised by the magnets used in the MAR medical brace 10. The magnets may cause magnetic interference, which can reduce the clarity of transmission from the wireless transmitter 46 and potentially damage the data recorded on the data recorder 50. Since the control mechanism 40 will be subject to magnetic interference from the magnets and/or electromagnets, at least the wireless transmitter 46 and the data recorder 50 are preferably magnetically shielded to overcome potential magnetic interference.

While the above describes some of the user or patient defined adjustment of the stiffness of the MAR medical brace 10, the control mechanism 40 includes programming capabilities that may be preset by the physician or possibly the user. For example, the physician may program the MAR medical brace 10 via the processor 42 to gradually decrease the magnetic strength from the magnet packs 30 over the course of the recommended healing or recovery time. This results in the stiffness or rigidity of the MAR medical brace 10 gradually decreasing as the patient heals and grows stronger over time, which eliminates frequent visits with the physician for similar adjustments. Moreover, the wireless transceiver 46 may also function as a receiver in order to receive programs, physician directed adjustments and other commands remotely. In the case of the MAR medical brace 10 being worn for sports or recreational physical activity, the MAR medical brace 10 may be programmed by the user to increase the stiffness over a user-defined period of time so that proper support is maintained as the user becomes physically fatigued from that activity. This relieves constant manual readjustments from the user.

Figure 3:
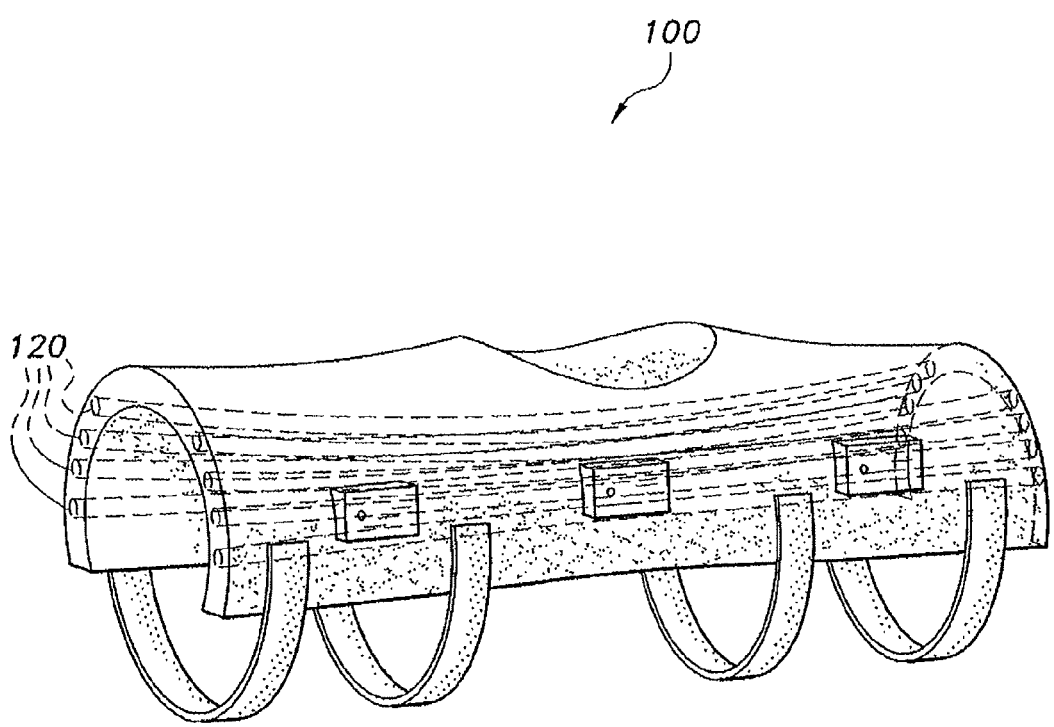
FIG. 3 is a perspective view of an alternative embodiment of a magnetorheological medical brace.
Figure 4:
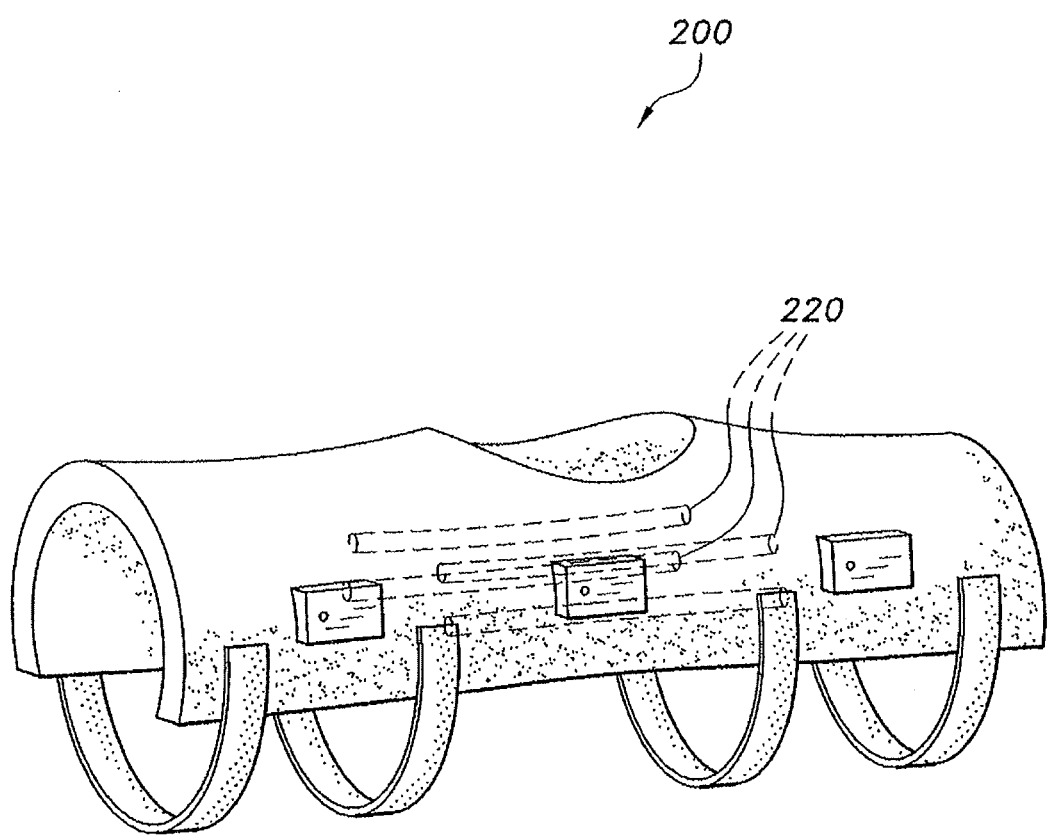
FIG. 4 is a perspective view of another alternative embodiment of a magnetorheological medical brace.
Figure 5:
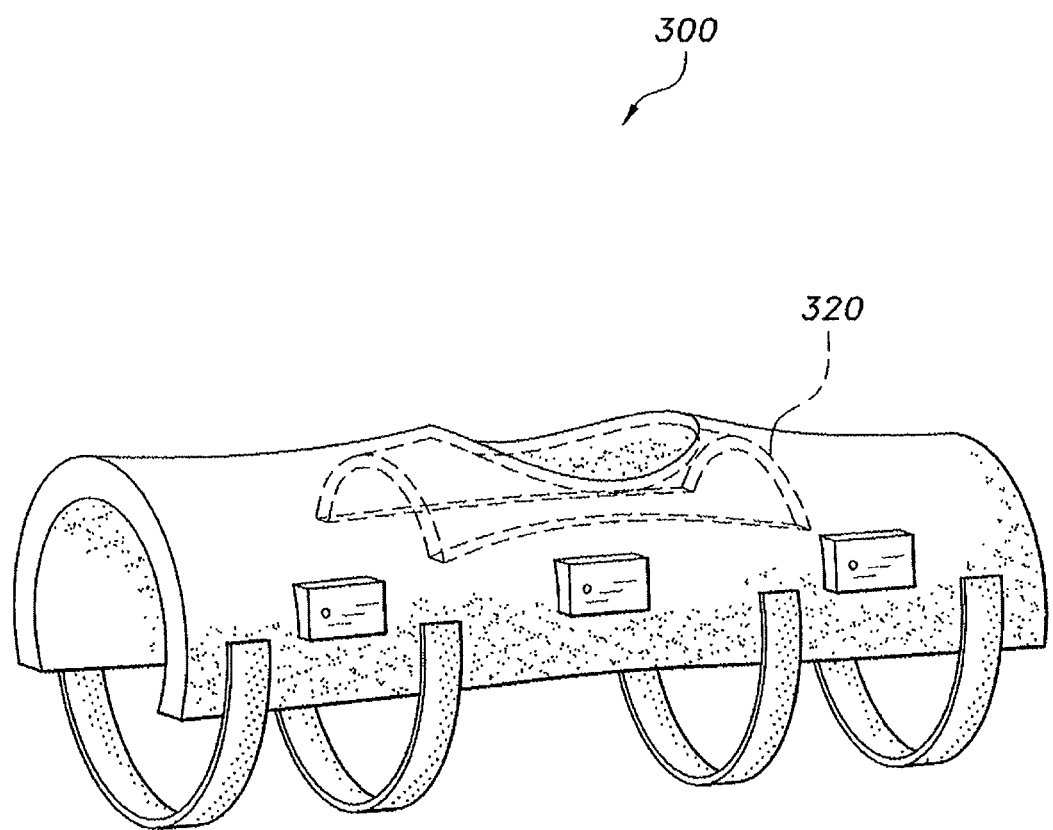
FIG. 5 is a perspective view of a still further alternative embodiment of a magnetorheological medical brace.

Referring to FIGS. 3-5, these drawings show alternative arrangements of the MAR pack for selective reinforcement of the brace. In FIG. 3, the MAR medical brace 100 in the form of a leg brace includes a plurality of MAR packs 120 embedded in the shell. The MAR packs 120 are shaped as elongate rods for longitudinal reinforcement of the MAR medical brace 100. The MAR packs 120 are removably inserted into the shell. As an alternative, the elongate MAR packs 120 may be molded with the shell. In FIG. 4, the MAR medical brace 200 includes a plurality of relative short MAR packs 220 disposed inside the shell. These MAR packs 220 may be placed in a variety of select locations on the MAR medical brace 200 wherever selective stiffening is desired. In FIG. 5, the MAR medical brace 300 includes a MAR pack 320 that is relatively smaller than the one shown in FIG. 2. The configuration thereof provides adjustable stiffness in a localized area around the joint. The variety of different MAR pack configurations is subject only to the changing needs of the patient.

Thus, it can be seen that the MAR medical brace 10, 100, 200, 300 is a highly adjustable brace that promotes optimum healing, convenience and comfort for the user. The MAR packs 20, 120, 220, 320 provide an easy and simple means of adjusting the stiffness and rigidity of the brace for increased comfort and freedom of movement as needed while maintaining the necessary support. The unitary and relatively simple construction also allows the MAR medical brace 10, 100, 200, 300 to be easily and inexpensively manufactured. In addition, the control mechanism 40 provides increased functionality whereby the patient's progress can be easily monitored and tailored to the individual.

It is to be understood that the MAR medical brace 10, 100, 200, 300 encompasses a variety of alternatives. For example, although the exemplary embodiments above describes the MAR medical brace 10, 100, 200, 300 in terms of a leg brace, it is to be understood that the teachings thereof equally applies to all types of braces. Moreover, the control assembly 40 is not limited to being installed in one of the magnet packs 30. Instead, the control assembly 40 can be a separate module or remote that can be carried by the user. Furthermore, it is to be understood that the MAR medical brace 10, 100, 200, 300 is not limited to human subjects or patients. The MAR medical brace 10, 100, 200, 300 may also be used on other subjects, such as animals.

It is to be understood that this disclosure is not limited to the embodiments described above, but encompasses any and all embodiments within the scope of the following claims.

What is claimed:

1. A magnetorheological (MAR) brace, comprising:
a flexible outer shell having an ergonomic shape adapted to be proximate to an area of a user's anatomy;
at least one MAR pack disposed inside the outer shell, the at least one MAR pack being filled with magnetorheological material, the magnetorheological material comprising a combination of at least carbonyl iron powder and silicone oil and wherein the at least one MAR pack further comprises a plurality of elongate rod-shaped packets disposed at select locations inside the flexible outer shell, the plurality of elongate rod-shaped packets providing longitudinal structural reinforcement for the flexible outer shell;
a plurality of magnets attached to the outer shell, the magnets exposing the MAR pack to magnetic field forces adjustably stiffening or loosening the magnetorheological material; and
a programmable control mechanism programmed by a physician to gradually decrease a degree of stiffness of the outer shell over a period of time by adjusting a magnetic field strength of the magnets.

2. A magnetorheological (MAR) brace, comprising:
a flexible outer shell having an ergonomic shape adapted to be proximate to an area of a user's anatomy;
at least one MAR pack disposed inside the outer shell, the at least one MAR pack being filled with magnetorheological material, the magnetorheological material comprising a combination of at least carbonyl iron powder and silicone oil and wherein the at least one MAR pack further comprises a plurality of short, elongate rod-shaped packets disposed at select locations inside the flexible outer shell, the plurality of short, elongate rod-shaped packets providing structural reinforcement for the flexible outer shell at select locations thereof;
a plurality of magnets attached to the outer shell, the magnets exposing the MAR pack to magnetic field forces adjustably stiffening or loosening the magnetorheological material; and
a programmable control mechanism programmed by a physician to gradually decrease a degree of stiffness over a period of time by adjusting a magnetic field strength of the magnets.

3. A magnetorheological (MAR) brace, consisting essentially of:
a relatively stiff or rigid outer shell having an ergonomic shape adapted to be proximate to an area of a user's anatomy;
at least one MAR pack removably disposed inside the outer shell for selective reinforcement thereof, the at least one MAR pack being filled with magnetorheological material;
a plurality of magnets attached to the outer shell, the magnets exposing the MAR pack to magnetic field forces adjustably stiffening or loosening the magnetorheological material;
a programmable control mechanism for selectively adjusting a magnetic field strength of the magnets, wherein selective adjustment of the magnetic field strength of the magnets increases or decreases a degree of stiffness of the outer shell;
wherein the programmable control mechanism is connected to a power source; and
a sensor for generating data, means for recording data from the sensor, and a means for wireless transmission of the data.

* * * * *